United States Patent [19]

Souza

[11] Patent Number: 4,666,839

[45] Date of Patent: May 19, 1987

[54] METHODS AND MATERIALS FOR OBTAINING MICROBIAL EXPRESSION OF POLYPEPTIDES INCLUDING BOVINE PROLACTIN

[75] Inventor: Lawrence M. Souza, Thousand Oaks, Calif.

[73] Assignee: Amgen, Thousand Oaks, Calif.

[21] Appl. No.: 445,986

[22] Filed: Dec. 1, 1982

[51] Int. Cl.[4] .................. C12P 19/34; C12P 21/00; C12P 21/02; C12N 15/00; C12N 1/00; C07H 17/00

[52] U.S. Cl. .................. 435/91; 435/172.3; 435/68; 435/70; 435/317; 536/27; 935/8; 935/10; 935/16; 935/17; 935/18

[58] Field of Search ............... 435/91, 172.3, 70, 68, 435/317; 536/27; 935/6, 8, 10, 13, 16, 17, 18

[56] References Cited

U.S. PATENT DOCUMENTS 4,293,652 10/1981 Cohen ........................ 536/27 X
4,342,832 8/1982 Goeddel et al. ............ 435/172.3
4,394,443 7/1983 Weissman et al. ............ 935/8 X

FOREIGN PATENT DOCUMENTS 0054330 6/1982 European Pat. Off. ......... 435/172.3
0054331 6/1982 European Pat. Off. ......... 435/172.3

OTHER PUBLICATIONS

Rothstein et al, in Methods in Enzymology, vol. 68, (Wu, Ed.), pp. 98–109 (1979).
Lewin, B., *Gene Expression*, vol. 3, pp. 621–623 and 752–758.
Maniatis, T. et al, Molecular Cloning, pp. 51–53 and 140.
Sasavage, N. L. et al., *J. Biol. Chem.*, vol. 257, No. 2, pp. 678–681, 1982.
Beaucage, et al., *Tetrahedron Letters*, 22: 1859–1962 (1981).
Gillam, et al., *Gene*, 12: 129–137 (1980).
Goeddel, *Nucleic Acids Research*, 8: 4057–4074 (1980).
Goeddel, et al., *Nature*, 281: 544–548 (1981).
Hu, et al., *Gene*, 17: 271–277 (1982).
Hunter, et al., *Nature*, 194: 495–496 (1962).
Keshet, et al., *Nucleic Acids Research*, 9: 19–30 (1981).
Matteucci, et al., *J. Am. Chem. Soc.*, 103: 3185–3191 (1981).
Messing, et al., *Gene*, 19: 269–276 (1982).
Montell, *Nature*, 295: 380–384 (1982).
Okayama, et al., *Mol. Cell. Biol.*, 2: 161–170 (1982).
Rupp, et al., *J. Mol. Biol.*, 61: 25–44 (1971).
Sancar, et al., *J. Bacteriol.*, 137: 692 (1979).
Sasavage, et al., *J. Biol. Chem.*, 257: 678–681 (1982).
Worcel, et al., *J. Mol. Biol.*, 82: 91–105 (1974).
Zettner, et al., *Clin. Chem.*, 20: 5–14 (1979).

*Primary Examiner*—Alvin E. Tanenholtz
*Assistant Examiner*—Jayme A. Huleatt
*Attorney, Agent, or Firm*—Marshall, O'Toole, Gerstein, Murray & Bicknell

[57] ABSTRACT

Disclosed are methods for selective modification of double-stranded DNA sequences facilitating their storage and incorporation into expression vectors. Manufactured partially double-stranded DNA primers are hybridized to complementary regions of single-stranded forms of DNA sequences to be altered. Desired, selectively modified double-stranded DNA sequences are then formed by DNA polymerization and specific nuclease digestion of undesired double- and single-stranded regions. Illustratively provided are DNA sequences useful in the microbial expression of bovine prolactin and other valuable polypeptides such as avian growth hormone.

12 Claims, 4 Drawing Figures

METHODS AND MATERIALS FOR OBTAINING MICROBIAL EXPRESSION OF POLYPEPTIDES INCLUDING BOVINE PROLACTIN

BACKGROUND

The present invention relates generally to the manipulation of genetic materials and more particularly to the use of recombinant procedures to selectively modify double-stranded DNA sequences, especially cDNA sequences, for storage and incorporation into expression vectors.

The development of specific DNA sequences for insertion into DNA vectors in an attempt to secure microbial expression of polypeptides encoded thereby is accomplished by a variety of techniques. Three principal methods for obtaining DNA sequences are: (1) the chemical manufacture of DNA sequences; (2) the isolation of double-stranded DNA sequences from donor DNA; and (3) the in vitro synthesis of double-stranded DNA sequences by reverse transcription of messenger RNA isolated from donor cells. The latter methods involve formation of a DNA complement of messenger RNA and are referred to as "cDNA" or "copy DNA" methods.

Chemical manufacture of polypeptide-specifying DNA sequences is clearly a method of choice, provided the amino acid sequence of the polypeptide to be microbially expressed is known and efficient synthetic procedures can be applied in the assembly of the sequence. (See, e.g., Stabinsky, U.S. patent application Ser. No. 375,493, filed May 6, 1982; and Alton, et al., U.S. patent application Ser. No. 375,494, filed May 6, 1982).

When double-stranded DNA sequences are chemically manufactured, it is seldom the case that significant difficulties are encountered either in storing the manufactured sequences in a convenient vector (such as the E.coli DNA plasmid, pBR322) or in inserting the sequences into functional expression vectors wherein their microbial transcription into mRNA is placed under the control of selected promoter/regulator sequences, transcription termination sequences, and the like. This is so because designs for chemical manufacture of polypeptide synthesis-directing DNA sequences can rather easily be adapted to incorporate initial and terminal sequences specifying, e.g., microbial mRNA translation initiation sequences, microbial mRNA translation termination sequences, and DNA sequences providing recognition sites for restriction endonuclease enzyme cleavage which will facilitate storage and/or insertion of the sequence into selected expression vectors.

Where the sequence of the polypeptide to be expressed is unknown, and in cases when chemical manufacturing procedures are not efficiently practiceable, resort must be made to donor DNA isolation and cDNA procedures to obtain desired DNA sequences. Such sequences are seldom in condition for ready incorporation into microbial expression vectors. It is almost invariably the case that the isolated sequence must be processed at its 5' end either to delete base pairs coding for an undesired polypeptide leader region or to insert base pairs coding for microbial translation initiation. Similarly, where the isolated sequence includes at its 3' end base pairs coding for an undesired terminal polypeptide region, these must ordinarily be deleted and an appropriate translation termination sequence must be inserted. Further, it is almost invariably the case that DNA sequences will need to be added to the isolated sequence to allow the storage (and amplification) in a vector or the insertion of the isolated sequence into an expression vector in the correct reading frame and location relative to a promoter/regulator region and/or transcription termination sequence.

A number of procedures have been developed in the art for performing selective modifications on double-stranded sequences. U.S. Pat. No. 4,342,832, for example, describes construction of cloning vehicles wherein a cDNA gene coding for a desired polypeptide is placed under the control of a selected expression promoter. Briefly stated, the cDNA sequence is analyzed for the presence of a unique restriction endonuclease recognition site near the 5' end and cleaved at such a site, effectively deleting undesired sequences (5' to the structural gene) along with at least a part of the desired polypeptide coding region. A chemically manufactured DNA sequence is then employed as a replacement for the lost polypeptide coding region and this manufactured sequence will ordinarily include a translation initiating sequence and desired recognition sites to facilitate incorporation into an expression vector. The same types of manipulations can be performed to secure modification of the 3' end of the cDNA sequence.

In the absence of one or more unique recognition sites in the DNA sequence to be modified, of course, the procedures of U.S. Pat. No. 4,342,832 cannot be performed. Further, even where such recognition sites are available, practice of the methods may require chemical synthesis of very long double-stranded DNA sequences as replacements for deleted polypeptide coding sequences and may therefore involve nearly as much work as total gene synthesis.

Of interest to the background of the invention are those publications treating the use of single-stranded DNA "primers" for isolating selected cDNA sequences and for effecting nucleotide base changes in central and terminal portions of double-stranded DNA sequences. See, e.g., Montell, C., et al., Nature, 295: 380–384 (1982): Gillam, S., et al., Gene, 12: 129–137 (1980); Goeddel, D., Nucleic Acids Research, 8: 4057–4074 (1980); and Hu, N., et al., Gene, 17: 271–277 (1982).

Of particular interest to the background of the invention are recently-published European Patent Application Nos. 054330 and 054331, which illustrate use of primers in methods for modifying double-stranded cDNA sequences. According to the illustrated methods, the DNA sequence coding for "mature" thaumatin is isolated from the central portion of a larger sequence coding for preprothaumatin by a series of manipulations involving use of single-stranded primers. The single-stranded primers are hybridized to single-stranded portions of the mature thaumatin sequence which have been isolated from the preprothaumatin double-stranded sequence by, e.g., denaturation. DNA polymerase and S1 endonuclease digestion are employed to provide a sequence having, at its 5' end, codons specifying the initial amino acids of mature thaumatin and, at its 3' end, a translation termination codon

5-TGA-3
3-ACT-5

In order to incorporate such a modified sequence into an expression vector, it must be immediately associated by blunt-end ligation with one or more synthetic, double-stranded, "linker" DNA sequences providing a translation initiation codon and/or a recognition site suited for proper insertion into the expression vector. (See, FIG. 4 of 054330 and FIG. 13 of 054331). Significant disadvantages attend use of the procedures illustrated. First, no means is provided for developing a selected terminal double-stranded sequence apart from performing a separate reaction with a linker. Second, no means is provided for "storage" or amplification of the modified double-stranded DNA sequence. Each modifying procedure must therefore be followed at its completion by association with a synthetic linker. If insertion into two different expression vectors is desired, for example, the modification procedures must essentially be duplicated in their entirety.

That the above-noted examples of procedures for selective modification of double-stranded DNA sequences are not readily and easily applied is evidenced by the fact that numerous cDNAs coding for commercially important polypeptides have been isolated and sequenced but have not as yet been successfully employed to effect microbial expression of the polypeptides. As one example, Sasavage, et al., *J. Biol.Chem.*, 257: 678–681 (1982) reports on the preparation, isolation, and sequencing of a double-stranded DNA coding for the 199 amino acid polypeptide sequence of bovine prolactin along with an approximately 30 amino acid untranslated leader region. However, the authors did not report microbial expression of bovine prolactin.

There exists, therefore, a substantial need in the art for improved methods and materials for selective modification of double-stranded DNA sequences, especially cDNAs, allowing for their storage and their incorporation into expression vectors. Such methods could be illustratively applied to readily secure the microbial expression of commercially significant polypeptides such as bovine prolactin.

BRIEF SUMMARY

The present invention provides novel, multi-step methods for selective modification of double-stranded DNA sequences facilitating their storage and incorporation into expression vectors. Briefly put, manufactured single-stranded or partially double-stranded DNA "primers" are hybridized to complementary regions of single-stranded forms of DNA sequences to be altered. Desired, selectively modified double-stranded DNA sequences are then formed by DNA polymerization and nuclease digestion of undesired double- and single-stranded regions.

Where the modification desired is simply the provision of one or two blunt ends facilitative of insertion into a storage vector, only a single-stranded primer need be used. Where it is desired to incorporate a transcription initiation or termination codon and/or where one or two entire restriction enzyme recognition sites are to be provided which will facilitate insertion into, e.g., an expression vector, the present invention dictates use of a partially double-stranded primer.

Procedures of the invention for modifying a double-stranded DNA sequence using a single-stranded primer include the following initial steps:

(1) forming a first selected single-stranded DNA copy of the double-stranded DNA sequence;

(2) hybridizing the first selected single-stranded copy to a manufactured single-stranded DNA sequence which is (a) complementary to a selected portion of the first selected single-stranded copy; and (b) has as the initial bases of its 5' end bases which, when complemented, form half of a recognition site for cleavage by a blunt-end-forming restriction endonuclease; and, (3) incubating the hybridized product of step (2) with nucleotide triphosphates and DNA polymerase under conditions facilitative of 3' extension of the manufactured sequence with bases complementary to the first selected single-stranded DNA copy, whereby the original double-stranded DNA sequence is reconstructed except for its sequence 3' to the site of hybridization of the selected single-stranded copy to the 5' end of the manufactured sequence.

If it is desired to isolate double-stranded DNA with half a blunt-end restriction enzyme recognition site at one of its ends, the following two additional steps are performed on the product of step (3):

(4) treating the product of step (3) to delete remaining single-stranded sequences 3' to the site of hybridization of the selected single-stranded copy to the 5' end of the manufactured sequence; and, (5) recovering the desired selectively modified double-stranded DNA sequence.

If it is desired to modify the double-stranded DNA so that it has halves of blunt-end recognition sites at each of its ends, the following additional steps are performed:

(6) forming a second selected single-stranded DNA copy of the modified double-stranded DNA sequence of step (5), the second selected single-stranded copy being the partial complement of the first selected single-stranded copy of step (1); and, (7) repeating steps (2), (3), (4), and (5) on the second selected single-stranded copy of step (6).

In the above procedures the 5' end of the manufactured single-stranded DNA sequence preferably contains bases which, when complemented, provide a half of a recognition site for a restriction endonuclease enzyme such as PvuII, HpaI, BalI, SmaI, HaeIII, AluI, NaeI or StuI, which are likely to correspond to unique restriction enzyme recognition sites in common DNA vectors such as pBR322. The manufactured single-stranded DNA sequence is desirably in the range of from about ten to about twenty bases in length and preferably about twelve.

Procedures of the invention for modifying a double-stranded sequence using a partially double-stranded primer include the following five initial steps:

(1) forming a first selected single-stranded DNA copy of the double-stranded DNA sequence;

(2) hybridizing the first selected single-stranded copy to a manufactured DNA sequence which comprises (a) a single-stranded portion complementary to a selected portion of the first selected single-stranded copy; and, (b) a double-stranded portion having a free end and an end wherein one strand is joined to the single-stranded region, which double-stranded portion includes base pairs forming a recognition site for cleavage by a restriction endonuclease enzyme and/or includes at its free end base pairs forming half of a recognition site for cleavage by a blunt-end-forming restriction endonuclease;

(3) incubating the hybridized product of step (2) with nucleotide bases and DNA polymerase under conditions facilitative of 5' to 3' extension of the single-stranded portion of the manufactured sequence with bases complementary to the first selected single-stranded DNA copy, whereby the original double-stranded DNA sequence is reconstructed except for its sequence 3' to the site of hybridization of the selected single-stranded copy to the 5' end of the single-stranded portion of said manufactured sequence;

(4) treating the product of step (3) to delete single-stranded sequences 3' to the site of hybridization of the selected single-stranded copy to the 5' end of the single-stranded portion of the manufactured sequence; and, (5) recovering the desired selectively modified double-stranded DNA sequence.

If the original double-stranded DNA is to have similar modifications at both ends, the following additional steps are performed:

(6) forming a second selected single-stranded DNA copy of the modified double-stranded DNA sequence of step (5), the second selected single-stranded DNA copy being the partial complement of the first selected single-stranded copy of step (1); and, (7) repeating steps (2), (3), (4), and (5) on the second selected single-stranded copy of step (6).

Where the 5' end of a double-stranded sequence is to be modified, the double-stranded portion of the manufactured DNA primer sequence may also include a

5'-ATG-3'
3'-TAC-5' transcription initiation codon. Where the 3' end of a double-stranded sequence is to be modified, the double-stranded portion of the primer may also include

5'-TGA-3'
3'-ACT-5' or similar transcription termination codon. Where the double-stranded portion of the primer includes base pairs providing an entire recognition site for restriction endonuclease cleavage, the site is generally one which corresponds to a unique recognition site present in a projected expression vector. When the double-stranded portion is to include at its free end base pairs forming half a blunt-end restriction enzyme recognition site (for insertion of the modified sequence into a storage vector), it is preferred that they be those associated with PvuII, HpaI, BalI, SmaI, HaeIII, AluI, NaeI, or StuI.

The length of the manufactured partially double-stranded primer may range from about ten to about twenty bases in its single-stranded region and from about ten to about twenty base pairs in its double-stranded region.

Use of filamentous bacteriophages such as M13 or the like substantially facilitates practice of procedures of the invention irrespective of whether single-stranded or partially double-stranded primers are employed. Further, it is within the comprehension to employ single-stranded priming procedures to effect a modification at one end of a double-stranded DNA sequence and partially double-stranded priming procedures to effect modification of the other end.

A further aspect of the present invention is the provision of a DNA sequence comprising base pairs arranged in codons specifying the amino acid sequence of bovine prolactin, wherein the initial base pairs of the protein coding sequence are

```
        Thr Pro Val
    5' ACA CCA GTC 3'
    3' TGT GGT CAG 5'
```

The DNA sequence may also include a

5'-ATG-3'
3'-TAC-5' codon, for transcription initiation.

Yet a further aspect of the present invention is provision of microbial expression vectors comprising a DNA sequence coding for bovine prolactin and microbial cells stably transformed with such vectors.

Cultivation of transformed microorganisms results in microbially expressed polypeptides having the biochemical properties of bovine prolactin.

Further aspects and advantages of the present invention will be apparent upon consideration of the following detailed description of the practice of preferred embodiments thereof, wherein.

DETAILED DESCRIPTION

Figure 1:
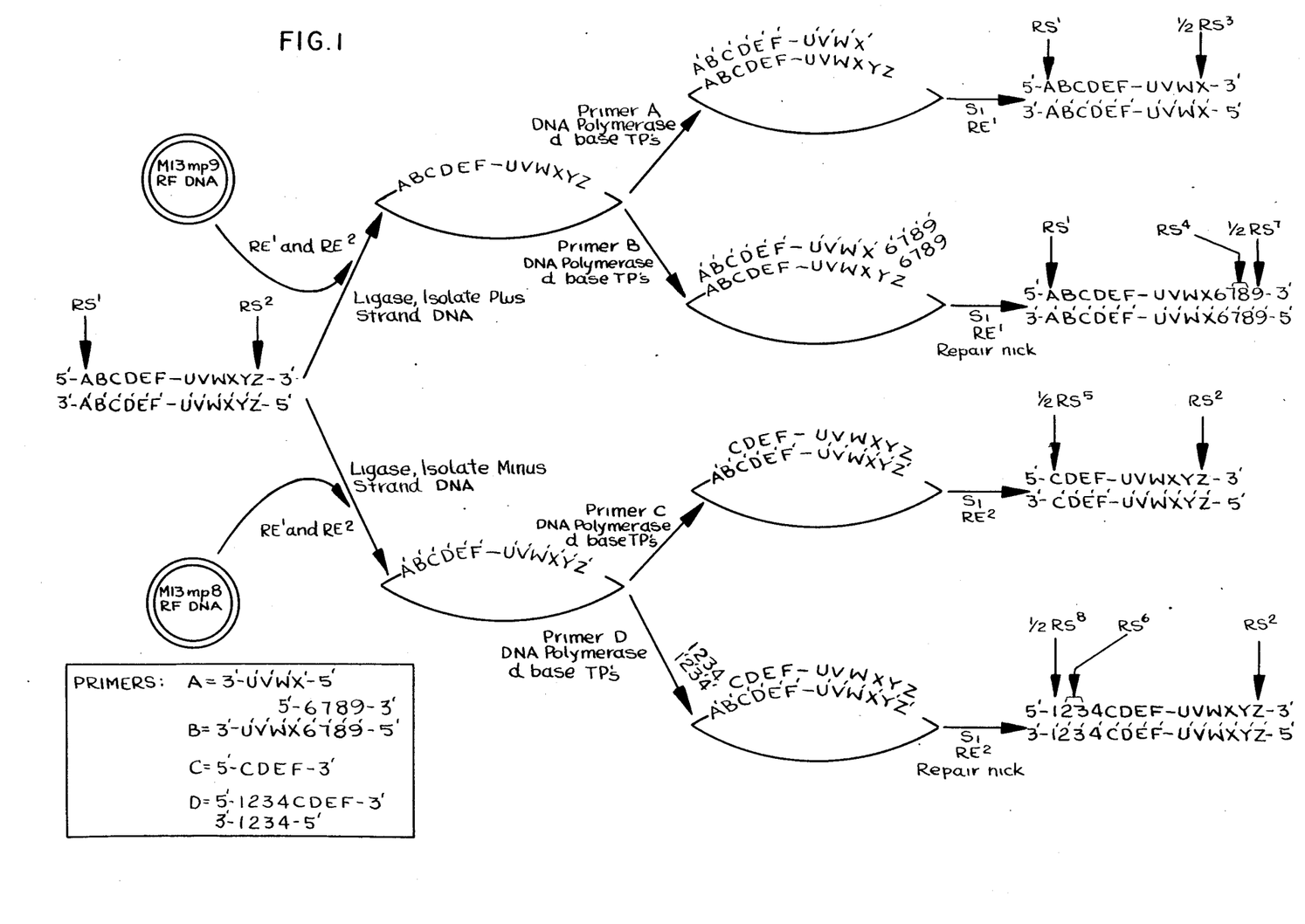
FIGS. 1 and 2 are schematic diagrams illustrating the various modifications to double-stranded DNA by the manipulations of the method of the present invention.
Figure 2:
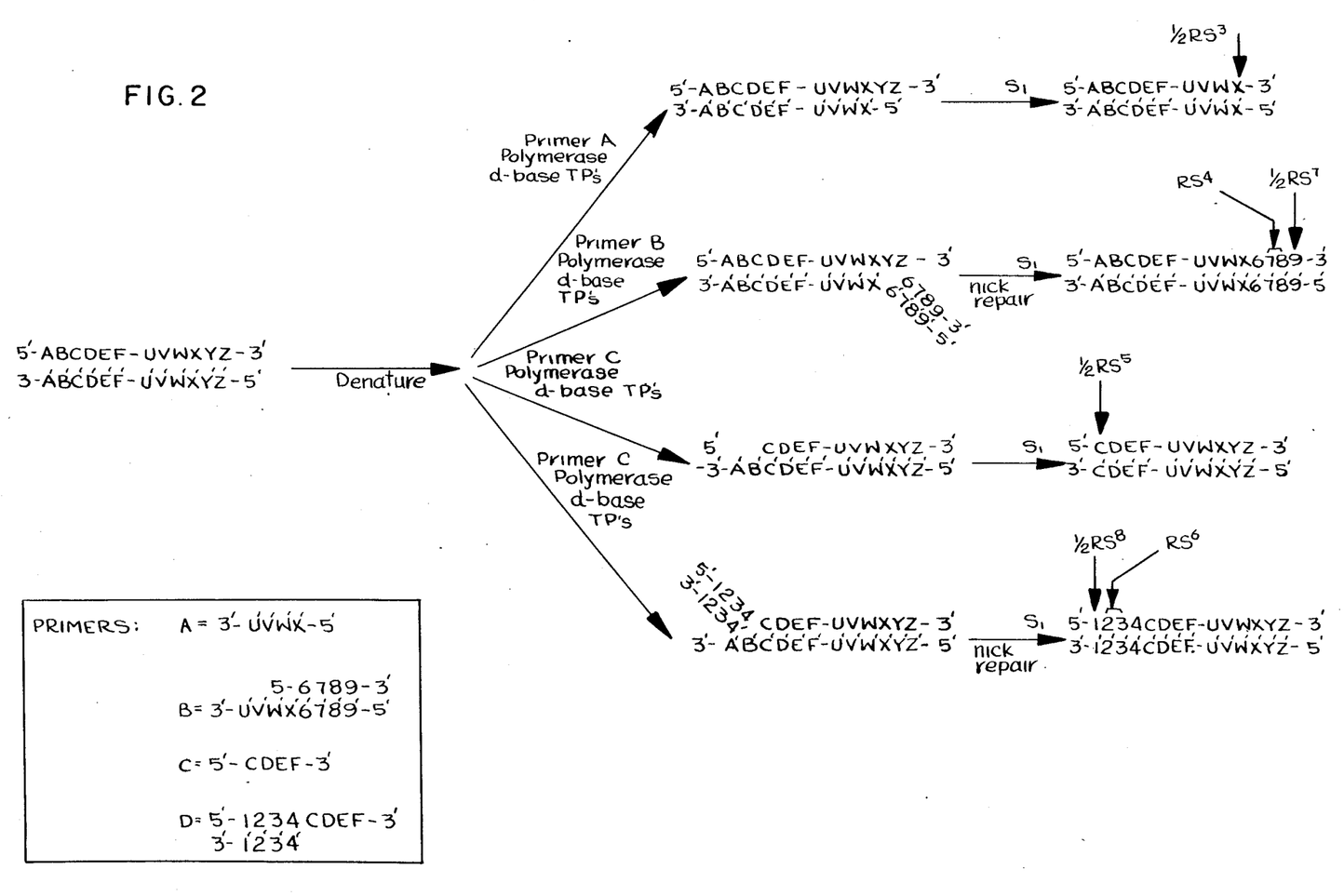

The methods of the present invention can be best understood through reference to schematic FIGS. 1 and 2. For ease of illustration, each number and letter in the schematic sequences in each figure represents three bases. FIGS. 1 and 2 illustrate manipulations performed on a hypothetically donor-isolated or cDNA-derived double-stranded DNA sequence:

5'-A B C D E F——U V W X Y Z-3'
3'-A'B'C'D'E'F'——U'V'W'X'Y'Z'-5' wherein A' is the complement of A, B' is the complement of B, and so on.

By virtue of its having been isolated from donor DNA or produced by cDNA methods, the sequence to be modified will typically include recognition sites RS[1] and RS[2] for cleavage by blunt- or sticky-end-forming restriction endonuclease enzymes RE[1] and RE[2] at 5'-A -3'    5'-Z -3'
3'-A'-5' and 3'-Z'-5' respectively.

An initial step in the procedures of the invention is the formation of a selected single-stranded copy of the double-stranded DNA sequence to be modified. Because DNA polymerases utilized in further steps of the method will only permit primer extension in the 5' to 3' direction, if it is desired to modify the 5' end of the gene, the single-stranded copy selected must be the "minus", "non-coding" strand. If modification is desired for the 3' end of the gene, the single-stranded copy selected must be the "plus" or "coding" strand. Selection of the "plus" or "minus" single strand from the two single strands of opposite orientation forming the double-stranded DNA can be accomplished in several ways:

(a) In FIG. 1 of the single-stranded DNA copy is accomplished by use of filamentous single-stranded DNA M13 bacteriophages (which are shown in FIG. 1 in the double-stranded replicating form (RF DNA)). The single-stranded phage DNA of M13 is always the plus strand. However, either the plus or minus strand of a double-stranded insert DNA can be cloned by use of M13 vectors, mp8 and mp9. A poly linker which contains multiple recognition sites for cleavage by restriction endonuclease enzymes (e.g., RE¹ and RE²) for cloning foreign DNA fragments into M13 can be introduced into the bacteriophage DNA in one orientation in mp8 and the opposite orientation in mp9. (Messing, J. and Vreira, J., *Gene,* 19, 269–276 (1982)). The double-stranded DNA sequence is easily inserted into either the mp8 or mp9 bacteriophage (previously cleaved with RE¹, RE²) at the corresponding recognition sites by a ligase enzyme.

(b) In FIG. 2, the initial step of forming a selected single-stranded copy of the double-stranded DNA sequence is accomplished by denaturation of the double-stranded sequence. The denaturation (other than through use of bacteriophages) can occur through use of heat, chemical or mechanical treatment of the double strand, thereby creating a "pool" of both minus and plus single strands. See Goeddel, et al., *Nucleic Acids Research,* 8: 4057–4074 (1980). Isolation of the selected "plus" or "minus" single strand for treatment with the further steps of the method occurs upon addition of the manufactured primer sequence of step 2, which is composed of bases complementary to a strand of one orientation only. The strand without a complementary primer remains unhybridized and is thus not "selected".

In the second step of procedures involving single-stranded manufactured primers, the selected single-stranded copy, e.g., 5'-ABCDEF -UVWXYZ-3' (hereafter "plus" strand), is hybridized to a manufactured single-stranded DNA sequence, e.g., Primer A, represented by 3'-U'V'W'X'-5'. Primer A is complementary to a selected portion of the "plus" strand, 5'-UVXY-3', thereby forming the hybrid Alternatively, the selected single-stranded copy 3'-A'B'C'D'E'F'—U'V'W'X'Y'Z'-5' (hereafter "minus" strand) would be hybridized to manufactured Primer C, represented by 5'-CDEF-3', forming the hybrid Manufactured Primers A and C, and any single-stranded primer used in the method, are each desirably in the range of from about ten to about twenty bases in length. Primers A and C represent the preferred length of twelve bases. Manufactured primer sequences of less than ten bases generally tend to form unstable hybrids, which may dissociate at the room temperature required for subsequent primer extension. Manufactured primer sequences of more than twenty bases, while able to form hybrids with good stability, require time-consuming manufacturing processes, and may therefore be less practical for use in the method of the present invention.

Before the primer sequence is manufactured, the selected single-stranded copy is scanned for the presence of a naturally-occurring sequence of bases which, when complemented by a primer, can form half of a recognition site for cleavage by a blunt-end forming restriction endonuclease. The location of such a sequence on the single-stranded copy determines the point of hybridization of the manufactured primer.

Therefore, as the initial bases of one end of the primer used (X' for Primer A and C for Primer C) there are bases which, when complemented, form half of a selected recognition site (½RS³, ½RS⁵) for respective blunt end-forming cleavage by endonucleases RE³ and RE⁵. The number of initial bases coding for half of a recognition site on the manufactured primer sequence can vary depending upon the particular restriction endonuclease to be utilized in cleavage. For example, the recognition site for PvuII cleavage is formed of six base pairs, If the selected recognition site was identified for cleavage by PvuII, three initial bases on the primer single strand, when complemented, would code for half of the site necessary for blunt end-forming cleavage. For example, Primer A's 5' initial bases (X') would, upon hybridization, form the 3' half of the recognition site for PvuII, or 5'-C T G-3'. Primer C in FIG. 1 could have as its 5' initial bases (C) 5'-CTG-3' which, when complemented, would also form the 3' half of the recognition site for PvuII. Other recognition sites exist which are formed of four base pairs. However, four base pair recognition sites occur quite frequently in most conveniently employed plasmid DNA vectors and thus are of limited practical interest for the purposes of the present invention.

In the third step of the method, the hybrid Primer A-"plus" strand or hybrid Primer C-"minus" strand is incubated with deoxynucleotide base triphosphates (dBaseTP's) and DNA polymerase I (Klenow fragment). This incubation at room temperature for a specified period of time facilitates 5' to 3' extension of Primer A with bases complementary to the bases of the "plus" strand or 5' to 3' extension of Primer C with bases complementary to the bases of the "minus" strand.

The hybrid strands may be extended to any desired region along the length of the single-stranded copy to form a continuous double strand, with the length of the resulting double-stranded region depending upon the amount of time primer extension is allowed to continue.

When Primer A is employed, the original double-stranded DNA sequence is reconstructed, except for the single-stranded sequence (Y'Z') 3' to the site of hybridization of the "plus" strand with the 5' end of manufactured Primer A. Similarly, when Primer C is employed, the original double-stranded sequence is reconstructed as:

A fourth step in the method is treatment of the reconstructed double-stranded DNA sequence with an enzyme capable of digestion of single-stranded DNA sequences, such as S1 nuclease. The addition of S1 nuclease removes remaining single-stranded regions (XY or A'B'). Thus, after cleavage at the unmodified end with RE¹ or RE², a double-stranded DNA sequence is recovered which contains deletion modifications to its 3' or 5' end including half of a new recognition site (½RS³ or ½RS⁵) responsive to cleavage by endonuclease (RE³ or RE⁵). These modifications enable easy insertion of the 3' or 5' modified end of the gene into the complementary half of the recognition site in an expression vector for storage and amplification.

In addition to modifying one end of the double-stranded sequence, the methods of the present invention involving single-stranded primers also provide for modification of both ends. For example, after Primer A has been used to achieve the 3' modification of the original double-stranded sequence to

```
5'-A B C D E F——U V W X -3'
3'-A'B'C'D'E'F'——U'V'W'X'-5'
``` the modified double-stranded sequence can be inserted back into a bacteriophage RF DNA (cleaved with RE¹ and RE³), and the "minus" modified strand isolated therefrom. The modified minus strand could then be subjected to the same steps of the method using Primer C. Alternatively, where no complementary recognition sites exist in an available bacteriophage or other replicating vector, the modified double-stranded sequence can be denatured to separate the modified plus strand from the modified minus strand (FIG. 2). Use of Primer C to hybridize with the minus strand in the pool of plus and minus strands will enable primer extension of only the minus strand when in the presence of dBaseTP's and DNA polymerase. Subsequent treatment of the reconstructed double-stranded sequence with S1 nuclease will digest not only the remaining single-stranded regions on the reconstructed double-stranded sequence but also the single plus strands in the pool.

Practice of the method, therefore, also allows recovery of a double-stranded DNA sequence which contains modifications to both of its ends introduced by the manufactured single strand Primers A and C. The modification of both ends of the sequence to incorporate half of a restriction endonuclease recognition site on each end allows ready insertion of the modified DNA sequence into a vector with complementary recognition sites for storage and amplification.

Where selective modification of a double-stranded DNA sequence involves utilizing a manufactured partially duplexed primer, the selected single-stranded copy of the double-stranded DNA sequence is formed by the same procedures described above for use of the manufactured single-stranded primers, i.e., use of a single-stranded DNA bacteriophage (FIG. 1) or by denaturation (FIG. 2). The selected single-stranded sequence (e.g., the "minus" strand) isolated from M13mp8 or the denaturation pool is hybridized to manufactured DNA Primer D which includes (1) a single-stranded portion (5'-CDEF 3') complementary to a portion (3'-C'D'E'F'-5') of the selected minus single-stranded sequence and (2) a selected double-stranded portion

```
5'-1 2 3 4 -3'
3'-1'2'3'4'-5'
``` having a free end at

```
5'-1-
3'-1'-
``` and an opposing end, wherein strand 5'1234- is joined to the single-stranded portion 5'-CDEF 3'. The double-stranded portion of Primer D either includes base pairs

```
5'-2 3-3'
3'-2'3'-5'
``` forming a complete recognition site (RS⁶) for cleavage by a restriction endonuclease enzyme (RE⁶) and/or includes at

```
5'-1
3'-1'
``` half of a recognition site ½RS⁸ for cleavage by a blunt end-forming RE⁸.

In a like manner, a selected plus strand can be hybridized to Primer B including double-stranded portion

```
5'-6 7 8 9-3'
3'-6'7'8'9'-5'
``` providing the entire RS⁴ restriction endonuclease recognition site

```
5'-7 8-3'
3'-7'8'-5'
``` for cleavage by RE⁴ endonuclease and/or half a site ½RS⁷ for blunt-end cleavage by RE⁷.

The Primer D/minus strand hybrid or Primer B/plus strand hybrid sequence is incubated with deoxynucleotide base triphosphates and DNA polymerase, under conditions facilitative of 5' to 3' extension of the hybridized single-stranded portion. As in the previously-described methods, the extension length depends on the amount of time the reaction continues. In use of Primer D, this third step allows reconstruction of the double-stranded sequence except for

```
5'-A B-3'
3'-A'B'-5',
``` because this region is 3' (on the minus strand) to the site of hybridization at

```
5'-C-3'
3'-C'-5'.
```

When Primer B is used, the original sequence is reconstructed except for

```
5'-Y Z-3'
3'-Y'Z'-5'.
```

Further treatment of the reconstructed double-stranded DNA sequence with S1 nuclease deletes 3'-A'B'-5' or 5'-YZ-3' and any remaining single-stranded regions (i.e., the plus strand in the denaturation pool or single-stranded phage DNA). The reconstructed sequence is treated with S1 nuclease. RE¹ or RE² treatment yields either modified double-stranded DNA sequence,

```
5'-1 2 3 4 C D E F—U V W X Y Z-3'
3'-1'2'3'4'C'D'E'F'—U'V'W'X'Y'Z'-5' or
```

-continued

5'-A B C D E F—U V W X Y Z 6 7 8 9-3'
3'-A'B'C'E'F'—U'V'W'X'Y'Z'6'7'8'9'-5'.

The nick between bases 4' of Primer D and the adjacent bases C' of the minus strand or bases 6 of Primer B and adjacent bases X of the plus strand is repaired (e.g., when the modified double-stranded sequence is ligated into a bacterial vector by the action of an enzyme, such as T<sub>4</sub> ligase).

In a process analogous to that described for the single-stranded Primers A and C, the method for selective modification of a double-stranded DNA sequence by partially double-stranded primers can be varied to include modification of both ends of the double-stranded sequence. For example, the plus strand of the modified double-stranded sequence would be isolated, by M13mp9 or denaturation. Primer B in FIGS. 1 and 2 would be utilized in the steps of the method described above for modification of the 5' end, resulting in a double-stranded sequence modified at both ends, i.e.,

5'-1 2 3 4 C D E F—U V W X 6 7 8 9-3'
3'-1'2'3'4'C'D'E'F'—U'V'W'X'6'7'8'9'-5'.

Another advantage for use of double-stranded primer sequence like Primers D and B is that the primers enable the insertion of a methionine coding region 5' to the DNA sequence coding for a desired polypeptide (e.g., at position 4) to allow translation of the sequence and-/or a stop codon 3' to the DNA coding region (e.g., at position 6) to terminate translation when the modified double-stranded sequence is in an expression vector.

An example of use of the method of the present invention is the creation of an expression vector including a modified cDNA sequence which codes for the microbial synthesis of bovine prolactin hormone. The following Examples 1 through 4 demonstrate manipulations performed on a double-stranded DNA sequence containing the sequence coding for bovine prolactin hormone (bPRL) polypeptide:

(1) identification and isolation of cloned bPRL DNA sequences in pBR322-SV40 recombinants by use of a rat prolactin cDNA probe;

(2) formation and sequencing of single-stranded copies of bPRL sequences by use of phage M13;

(3) manufacture of a single-stranded primer sequence and its use in hybridization with the selected single-stranded sequence and primer extension to form a 5' modified sequence; and (4) further modification of the sequence of Example 3 for construction of a bacterial cell expression vector.

Example 5 relates to biochemical similarity of microbially-produced bPRL according to the invention and bovine prolactin purified from bovine pituitary glands. Example 6 describes a sequential competition radioimmunoassay employing the bovine prolactin polypeptide produced in cells transformed with plasmids harboring bPRL.

Another example of use of the method of the present invention are the manipulations performed on the DNA sequence coding for expression of growth hormone of the chicken species disclosed in applicant's co-pending patent application Ser. No. 418,846, filed Sept. 16, 1982. In that application, a high molecular weight polypeptide having the biochemical and immunological properties of growth hormone native to avians is disclosed. The construction of an illustrative bacterial cell expression vector cGH-T21 harbored in ATCC No. 39182 was the result of the manipulations of the present invention. Those manipulations are the subject of Examples 7 and 8 and FIGS. 3 and 4 following.

EXAMPLE 1

The nucleotide and predicted amino acid sequences of a cDNA coding for bovine prolactin was deduced by Sasavage, et al., supra. The described sequence is as follows:

```
5'
TGCTTGGCTGAGGAGCCATAGGACGAGAGCTTCCTGGTGAAGTGTGTTTCTTGAAATCATCACCACC

-30                                    -20
Met Asp Ser Lys Gly Ser Ser Gln Lys Gly Ser Arg Leu Leu Leu
ATG GAC AGC AAA GGT TCG TCG CAG AAA GGG TCC CGC CTG CTC CTG

-10
Leu Leu Val Val Ser Asn Leu Leu Leu Cys Gln Gly Val Val Ser
CTG CTG GTG GTG TCA AAT CTA CTC TTG TGC CAG GGT GTG GTC TCC

+1                                      10
Thr Pro Val Cys Pro Asn Gly Pro Gly Asn Cys Gln Val Ser Leu
ACC CCC GTC TGT CCC AAT GGG CCT GGC AAC TGC CAG GTA TCC CTT 20                              30
Arg Asp Leu Phe Asp Arg Ala Val Met Val Ser His Tyr Ile His
CGA GAC CTG TTT GAC CGG CGA GTC ATG GTG TCC CAC TAC ATC CAT

40
Asp Leu Ser Ser Glu Met Phe Asn Glu Phe Asp Lys Arg Tyr Ala
GAC CTC TCC TCG GAA ATG TTC AAC GAA TTT GAT AAA CGG TAT GCC 50                              60
Gln Gly Lys Gly Phe Ile Thr Met Ala Leu Asn Ser Cys His Thr
CAG GGC AAA GGG TTC ATT ACC ATG GCC CTC AAC AGC TGC CAT ACC

70
Ser Ser Leu Pro Thr Pro Glu Asp Lys Glu Gln Ala Gln Gln Thr
TCC TCC CTT CCT ACC CCG GAA GAT AAA GAA CAA GCC CAA CAG ACC 80                              90
His His Glu Val Leu Met Ser Leu Ile Leu Gly Leu Leu Arg Ser
CAT CAT GAA GTC CTT ATG AGC TTG ATT CTT GGG TTG CTG CGC TCC
```

```
                                          100
Trp Asn Asp Pro Leu Tyr His Leu Val Thr Glu Val Arg Gly Met
TGG AAT GAC CCT CTG TAT CAC CTA GTC ACC GAG GTA CGG GGT ATG 110                                        120
Lys Gly Ala Pro Asp Ala Ile Leu Ser Arg Ala Ile Glu Ile Glu
AAA GGA GCC CCA GAT GCT ATC CTA TCG AGG GCC ATA GAG ATT GAG

130
Glu Glu Asn Lys Arg Leu Leu Glu Gly Met Glu Met Ile Phe Gly
GAA GAA AAC AAA CGA CTT CTG GAA GGC ATG GAG ATG ATA TTT GGC 140                                        150
Gln Val Ile Pro Gly Ala Lys Glu Thr Glu Pro Tyr Pro Val Trp
CAG GTT ATT CCT GGA GCC AAA GAG ACT GAG CCC TAC CCT GTG TGG

160
Ser Gly Leu Pro Ser Leu Gln Thr Lys Asp Glu Asp Ala Arg Tyr
TCA GGA CTC CCG TCC CTG CAA ACT AAG GAT GAA GAT GCA CGT TAT 170                                        180
Ser Ala Phe Tyr Asn Leu Leu His Cys Leu Arg Arg Asp Ser Ser
TCT GCT TTT TAT AAC CTG CTC CAC TGC CTG CGC AGG GAT TCA AGC

190
Lys Ile Asp Thr Tyr Leu Lys Leu Leu Asn Cys Arg Ile Ile Tyr
AAG ATT GAC ACT TAC CTT AAG CTC CTG AAT TGC AGA ATC ATC TAC

199
Asn Asn Asn Cys  UC              *
AAC AAC AAC TGC TAA GCCCACATTCCATCCTATCCATTTCTGAGATGGTTCTTAAT

GATCCATTCCCTGGCAAACTTCTCTGAGCTTTATAGCTTTGTAATGCATGCTTGGCT
                                                              3'
CTAATGGGTTTCATCTTAAATAAAAACAGACTCTGTAGCGATGTCAAAATCTpolyA
```

To obtain the cDNA sequence coding for bovine prolactin, complementary DNA made from bovine pituitary mRNA was cloned into pBR322-SV40 vectors by the method of Okayama, H., and P. Berg, *Mol.Cell-.Biol.*, 2: 161-170 (1982). These recombinants were screened for the presence of bPRL sequences using a rat prolactin cDNA probe. The rat probe aligned with the homologous bovine prolactin sequences in the clones, thus enabling ready isolation of those clones containing bPRL. The clone containing the largest insert (bPRL8) of the eight found to hybridize to rat prolactin (rPRL) was chosen for further manipulations.

EXAMPLE 2

Insert bPRL8 was sequenced by the dideoxy method using M13-bPRL8 clones as templates. The sequence of bPRL8 revealed the following structural components of the gene:
(1) a 5' untranslated sequence of 50 bases,
(2) a 30 amino acid leader,
(3) a 199 amino acid mature protein, and
(4) a 3' untranslated sequence of 146 bases.
These findings are all consistent with those published by Sasavage, N. L., et al., *J.Biol.Chem.*, 257: 678-681 (1982), except for a few minor third base substitutions at amino acid numbers 67 and 76, and the absence of one C in the 3' untranslated region.

Specifically, the codon for amino acid number 67 (proline) was CCT, rather than CCG, as published; and for amino acid number 76 (histidine) CAC, rather than CAT. The C omitted is marked with an asterisk above it in the sequence above.

The entire bPRL sequence was not readily accessible for securing direct and optimal expression of bPRL in a microbial host due to the presence of the approximately 140 base sequence 5' to the bPRL coding region (which sequence presumptively codes for a 30 amino acid leader region) and a 5' untranslated region. In addition to deleting the 140 base sequence 5' to the first codon of the mature form of bPRL, to secure expression of bPRL the coding region should be provided with an initial

```
5' ATG 3'
3' TAC 5"
``` and inserted into a transformation vector at a site under control of a suitable promoter/regulator DNA sequence. Due to the presence of a recognition site for cleavage by the Sau3A endonuclease in the long 3' untranslated sequence, that sequence presents no obstacle to securing expression. The sequence can be partially deleted by treatment with Sau3A at the recognition site

```
5'-G A T C-3'
3'-C T A G-5'.
```

EXAMPLE 3

A primer sequence was manufactured for use in primer extension of a single-stranded copy of the bPRL sequence. The primer is synthesized by the amino phosphine method [Beaucage and Caruthers, *Tetrahedron Letters,* 22: 1859-1962 (1981)], on a solid support [Matteucci and Caruthers, *J.Am.Chem.Soc.*, 103: 3185-3191 (1981)], except that 3% trichloroacetic acid in nitromethane is used instead of zinc bromide for the detritylation step. The primer sequence was a synthetic fifteen base oligimer complementary to an M13mp8 clone containing the entire bPRL cDNA sequence. The primer begins at nucleotide position +9 with respect to the first amino acid of the mature protein and extends to nucleotide position +23. The primer therefore had the sequence:

5'-CTGT CCC AAT GGG CC-3'.

The selected M13 single-stranded DNA sequence for bPRL (1 μg) was hybridized to copies of this primer (a 5 molar excess) in H Buffer (6.6 mM Tris-HCl pH 7.5, 6.6 mM MgCl$_2$, 6.6 mM NaCl, and 5.0 mM dithiothreitol) at 85°–100° C. and allowed to slow cool to room temperature. The hybrid product was then incubated in the presence of deoxynucleotide base triphosphates (final concentration 0.5 mM each) and 1 unit of Klenow (large fragment of DNA polymerase I). The final reaction volume was 25 μl and incubation was carried out at room temperature for 20–30 minutes. This incubation time period allowed the primer sequence to be extended past the bPRL insert (past a Sau3A cleavage site) and partially around the M13 portion of the single-stranded clone. The primer extension reaction was stopped by the addition of 1.5 μl of 2% sodium dodecylsulfate (SDS) and then ¼ volume of 5× Buffer D (50 mM Tris pH 7.5, 250 mM NaCl, and 5 mM EDTA) was added. The reaction was then extracted with an equal volume of phenol:CHCl$_3$ (50:50), CHCl$_3$, and finally precipitated with ethanol. The reconstructed double-stranded DNA sequence was thereafter treated with S1 nuclease which digested the remaining single-stranded portions of the original M13 template 3' to the site of hybridization, including the 5' untranslated region through the nucleotide position +8 and the remaining single-stranded 3' region. The S1 reaction contained 50 mM KAc (pH 4.5), 200 mM NaCl, 1 mM ZnSO$_4$, 25–100 units SI and the primer elongated DNA in a 25 μl volume. The reaction was carried out at 15° C. for 30 minutes, then stopped and treated as described for the primer elongation reaction. The 5' end of the reconstructed double-stranded sequence now was initiated by three bases forming the 3' half of a recognition site for cleavage by PvuII. Further treatment with Sau3A endonuclease to cleave the now-duplexed untranslated 3' region at a Sau3A recognition site was accomplished by:

(1) resuspending DNA from the previous reaction in 21.5 μl H$_2$O;

(2) adding 2.5 μl of 10× Sau3A buffer (67 mM Tris pH 7.5, 67 mM MgCl$_2$, 500 mM NaCl and 67 mM mercaptoethanol); and (3) adding 0.6 μl of Sau3A (3 units) and allowing digestion to occur for 1 hour at 37° C.

This modified double-stranded sequence was recovered from the reaction as described for the previous reactions. A 3-to-5 molar excess of the modified DNA was ligated to 50–100 ng of pBR322 vector previously digested with BamHI and PvuII and gel purified. The DNA was then transformed into E.coli strain HB101 and the resulting transformants tested by plasmid analysis for the appropriate Sau3A and PvuII cleavage sites. One clone, bPRL13-2, contained the appropriate insert and was selected for further manipulations.

EXAMPLE 4

Construction of a vector for the direct expression of the mature form of bPRL was accomplished by further modification of the sequence developed in Example 3. An 18 base linker was manufactured containing 8 bases required to build back the first three codons of the bPRL-specifying DNA sequence, an ATG initiation codon, and bases providing an XbaI restriction site, which would enable cloning into a tryptophan (Trp) promoter of a pBR322-derived vector. The sequence of the linker was the following:

```
5'-CTAG AGA ATG ACA CCA GT-3'
3'-     TCT TAC TGT GGT CA-5'
```

In this linker, the 8 bases coding for nucleotide positions +1 through +8 differed from the original, cDNA bPRL sequence at nucleotide positions +3 and +6. The purpose of the two changes from C to A was to include E.coli preference codons for the required amino acids. A 3 molar excess of both the 18 base linker and the modified bPRL gene were ligated into a pBR322 derived Trp promoter vector (Pint-γ-txB4). The colonies isolated after transformation of E.coli which contain the appropriate insert configuration are capable of directing the synthesis of the mature form of bPRL.

Expression of a polypeptide having the biochemical properties of bPRL in E.coli was monitored by polyacrylamide gel electrophoresis of radiolabelled maxicells (Example 5) and by radioimmunoassay of crude bacterial lysates (Example 6).

EXAMPLE 5

The molecular weight of the microbially-produced bPRL polypeptide of the invention was determined by SDS-Polyacrylamide Gel Electrophoresis (SDS-PAGE) of $^{35}$S-methionine ($^{35}$S-met) labelled maxicells (CSR603) harboring plasmids carrying the bPRL gene. Briefly, the procedure involves growing 10 mls of CSR603 (bPRL) in K-media [Rupp, et al., *J.Mol.Biol.*, 61: 25–44 (1971)] to a concentration of 2×10$^8$ cells/ml. Five mls of cells are then irradiated in a 60 mm petri dish on a shaker platform with a UV dose of 1–5 J/m$^2$, and allowed to shake for one hour at 37° C., at which point cycloserine is added at 100 μg/ml. The cultures remain shaking for an additional 8–12 hours and cells are thereafter collected by centrifugation and washed twice with Herschey salts [Worcel, et al., *J.Mol.Biol.*, 82: 91–105 (1974)]. Cells are resuspended in 2.5 mls of Herschey media and incubated at 37° C. with aeration for one hour. 1 ml of cells are then placed in a 50 ml polypropylene tube with 50 μCi of $^{35}$S-met (New England Nuclear) and 10 μg of 3-indoleacrylic acid and then incubated for another hour at 37° C. Finally, cells are harvested, lysed and analysed by SDS-PAGE and autoradiography. This procedure had been designed so that nearly all the labelled $^{35}$S-met is incorporated into plasmid encoded gene products. [Sancar, et al., *J.Bacteriol.*, 137: 692 (1979)].

Two protein bands were detected after autoradiography of the gel. One protein, β-lactamase with a MW of 30,000, is present in all cultures resistant to ampicillin containing pBR322 derived plasmids. A second protein of approximately 24,000 MW is seen only in cultures containing the plasmids encoding the bPRL gene. The MW of the recombinant bPRL is similar to that found for the natural bovine prolactin purified from pituitary glands.

EXAMPLE 6

To determine the levels of bPRL expression, a sequential competition radioimmunoassay [Zettner, et al., *Clin.Chem.*, 20: 5–14 (1979)] was generated.

Samples of microbially produced bPRL are prepared for use in the RIA as follows:

Cells of *E. coli* K-12 strain HB101 containing the bPRL expression plasmid are grown in M9 minimal salts supplemented with 0.4% glucose, 1 mM $MgSO_4$, 0.1 mM $CaCl_2$, 5 mg/ml casamino acids and 10 μg/ml thiamine in a 37° C. shaker to an O.D. ($A_{600}$) of 1. At this point, 15 mls of cells are treated with 3-indoleacrylic acid (final concentration 10 μg/ml) and allowed to continue to shake at 37° C. for 1 hour. 10 mls cells are then pelleted at approximately 4,000×g in a Beckman J-6 and resuspended in 0.5 ml of a Tris-sucrose-lysozyme buffer (Goeddel, et al., *Nature*, 281, 544–548 [1981]) containing, in addition, 0.05% sodium dodecyl sulfate and 1 mM phenylmethylsulfonylfluoride. The cells are then placed on ice for 30 minutes after which they are treated with 0.11 ml of a DNase buffer and 10 μg of DNase I (Worthington) as described in Goeddel, et al. The supernate is then spun at 12,000×g for 15 minutes in an Eppendorf microfuge and the supernate is decanted into a tube containing 25 μl of 10% Triton X-100.

Purified bPRL isolated from bovine pituitaries was labelled with $^{125}I$ for use as tracer in the RIA using a modification of the chloramine-T reaction procedure described by Hunter and Greenwood, *Nature*, 194: 495–496 (1962). Briefly, the procedure involves combining 10 μg of bPRL in 10 μl of 0.05M bicarbonate buffer, pH 9.2, 50 μg chloramine T, and 500 μCi of sodium $^{125}I$ (approximately 17 Ci/mg) (New England Nuclear) in 50 μl of 0.2M tris-HCl, pH 7.2, 0.002M EDTA, and incubating for 1 minute at room temperature. Sodium metabisulfite (500 μg) is added to terminate the reaction and the mixture is loaded onto a 28 ml Sephadex G75 column previously washed with 0.1M phosphate saline (pH 8.0), 2% BSA, and 0.1M phosphate saline (pH 8.0), 0.1% BSA. Four 25-drop fractions are collected from the column and then 45–60 ten drop fractions.

Selected fractions containing radiolabelled material are tested for immune precipitability using the procedure of Keshet, et al., *Nucleic Acids Research*, 9, pp. 19–30 (1981). In this procedure, $2.5 \times 10^4$ cpm of iodinated bPRL is incubated with $1 \times 10^{-4}$ to $2 \times 10^{-4}$ dilutions of rabbit anti-bPRL in 0.5M Tris HCl (pH 8.9), 2.0% BSA, 0.1% Triton X-100, 0.1% SDS, for 2 hours at room temperature. Twenty microliters of 10% w/v formalin-fixed *Staphylococcus aureus* pre-washed with RIA buffer is then added and the mixture incubated for 20 minutes at room temperature. Immune precipitates are collected by centrifugation (12,000×g for 3 min.) and washed 3 times in RIA buffer before counting.

The most immune-precipitable column fractions are then used to construct a serum dilution curve using the same procedure as above, but employing serum dilutions over the range of $1 \times 10^{-3}$ to $1 \times 10^{-6}$. The serum dilution giving half maximal precipitation of $2.5 \times 10^4$ cpm of labelled bPRL is used in subsequent competition radioimmunoassays.

In those assays, $1 \times 10^{-6}$ to $1 \times 10^{-10}$ g of purified bPRL or to $10^0$ to $10^{-2}$ dilutions of bacterial lysates prepared as described above containing bPRL are pre-incubated with the appropriate dilution of anti-bPRL for 2 hours at room temperature, at which time $2.5 \times 10^{-4}$ to $3.5 \times 10^{-4}$ cpm of $^{125}I$-bPRL is added and the subsequent reactions, centrifugation and washing are accomplished as described above.

When the bacterial lysate bPRL is added to a fixed amount of anti-bPRL the appropriate immune complexes are formed. The fixed amount of labelled bPRL added to the reaction mixture complexes with any anti-bPRL not previously bound to the bacterial lysate bPRL competitor. The amount of radioactivity in the resulting precipitate is inversely proportional to the amount of bPRL competitor present in the sample.

Current levels of expression as measured by RIA are 0.2–0.4 mg/OD-L of cells. This immunoassay thus indicates that the bacterial lysates do, indeed, contain the DNA sequence capable of synthesizing a polypeptide exhibiting one or more of the biochemical characteristics of bovine prolactin including the ability of the polypeptide to form antigen-antibody complexes.

EXAMPLE 7

The procedure for obtaining the cDNA sequence coding for chicken growth hormone is described in detail in Applicant's co-pending application Ser. No. 418,846, filed Sept. 16, 1982, Examples 1 through 3, therein.

The single-stranded DNA phage M13 is used as a cloning vector for forming single-stranded DNA templates from the double-stranded cDNA coding for chicken growth hormone. The sequence of cGH reveals the following structural components of the gene, which can be seen in cGH5 of FIGS. 3 and 4:

(1) a 5′ untranslated sequence of 52 bases;
(2) a 26 amino acid leader;
(3) a 190 amino acid mature protein; and
(4) a 3′ untranslated sequence of approximately 100 bases.

The cDNA cGH sequence is not readily accessible for securing direct and optimal expression of the mature form of cGH in a microbial host due to the presence of the approximately 78 base sequence 5′ to the cGH coding region which sequence presumptively codes for a 26 amino acid leader region, and a 5′ untranslated region. To secure such expression the cGH coding region should be provided with an initial

5′-ATG-3′
3′-TAC-5′ codon, and inserted into a transformation vector at a site under control of a suitable promoter/regulator DNA sequence.

The sequence for approximately the first half (5′ terminus) of the cGH protein coding DNA single strand in M13 includes a single BamHI recognition site as illustrated below:

+1            +349 BamHI
5′-TCC CCT GCC ATG CCC CTC TCC . . . GAA GGG ATC CAA . . . 3′

Figure 3:
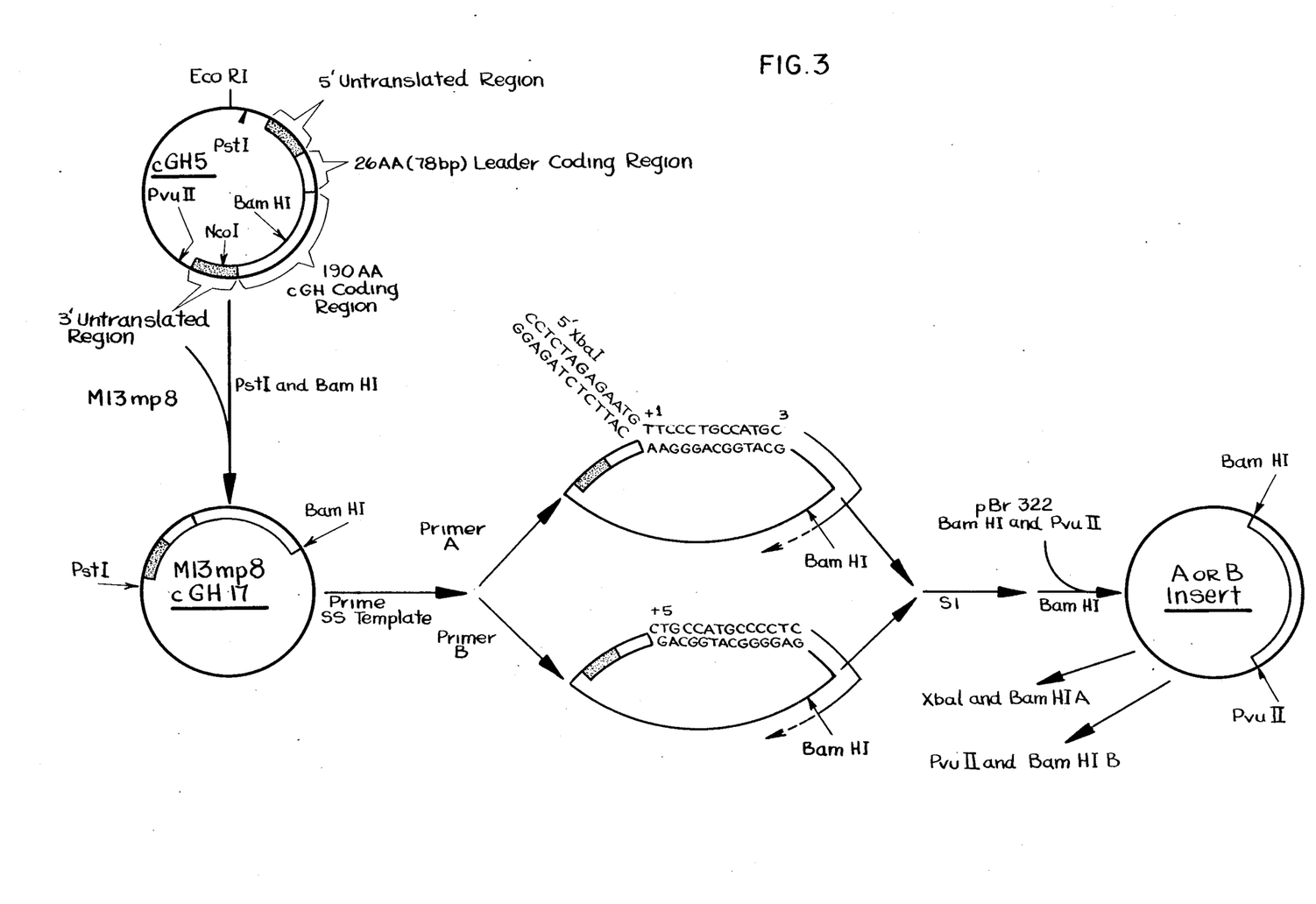
FIGS. 3 and 4 illustrate manipulations according to the invention involved in construction of expression vector cGH T21 harbored in ATCC No. 39182.

DNA inserts containing the 5′ portion of the cGH protein coding region (including an initial ATG and lacking bases coding for the leader sequence) may be prepared by the following method of the present invention using the single-stranded M13 DNA. As illustrated in FIG. 3, insert cGH5 containing the entire cGH gene is cleaved with endonucleases PstI and BamHI, which reaction produces two strands of cDNA, one strand containing the 5′ end of the cGH gene and a larger strand containing the 3′ end. The shorter strand is then incubated with and incorporated into single-stranded M13mp8 to form cGH17.

A. Insert No. 1

A partially duplexed DNA oligonucleotide primer is manufactured by the process described in Example 3. The partially double-stranded Primer A thus manufactured has the following sequence:

```
         XbaI
5'-C C T C T A G A G A A T G T T C C C T G C C A T G C-3'
3'-G G A G A T C T C T T A C-5'
```

This Primer A contains an XbaI site and an ATG adjacent the TTC phenylalanine codon. Two

```
5'-C
3'-G
``` base pairs are located at the beginning of the manufactured primer, providing a "safety region" to protect the XbaI restriction site in the primer sequence from digestion by S1 nuclease. The single-stranded M13 DNA (cGH17) containing the 5' terminus of the cGH gene (PstI-Bam HI) is incubated with the manufactured Primer A, whereby a hybrid double-stranded region is formed (see result of Primer A arrow in FIG. 3). A standard sequencing reaction using 1.0 μg of single-stranded DNA template from the M13 phage in a 25 μl reaction with DNA Polymerase I (Klenow) is carried out at room temperature for 20–30 minutes as described for bPRL. The short strand of the primer is in a threefold excess over the long strand to help assure that the primer remains as a duplex at its 5' terminus during S1 nuclease treatment. After this primer extension, the reaction is phenol-extracted, CHCl$_3$ extracted, and ethanol precipitated.

The DNA, now comprising the duplex primer 5' to 3' along the single-stranded M13 template approximately 1–2kb is re-suspended in an S1 nuclease buffer and subjected to the process described above for bPRL. The nick between Primer A base (C) and the original strand base (A) is repaired when the sequence is inserted into a bacterial vector by T$_4$ DNA ligase.

The double-stranded Primer A:cGH DNA is re-suspended in BamHI cleavage buffer (6 mM Tris, pH 7.4, 6 mM MgCl$_2$, and 150 mM NaCl) and digested with 10 units of BamHI in a 25 μl final volume at room temperature for 40 minutes, forming a BamHI sticky end on the 3' end (of the Primer A:cGH DNA). Upon completion of this reaction, the DNA is extracted and precipitated. pBR322 DNA cleaved with BamHI and PvuII is isolated from an agarose gel and ligated to a 5M excess of Primer A-synthesized DNA. The resulting transformants are tested by plasmid analysis for the XbaI site introduced by Primer A and the BamHI cleavage site. One clone, cGH16, (see FIG. 4) was selected for expression testing.

B. Insert No. 2

Another cGH insert containing the 5' portion of the gene suitable for incorporation into a storage vector is manufactured in a procedure similar to that of procedure A, above. Primer B in this case, however, contains no duplex portion and primes at a position 3' to the first codon of the cGH gene (see result of Primer B arrow in FIG. 3).

Primer B has the following sequence:

```
              PvuII
5'-C T G C C A T G C C C C T C-3'
```

A useful feature of this primer is that the 5' terminus contains the 3' half of a PvuII recognition site, so that following primer extension, treatment with S1 nuclease, and cleavage with BamHI, the resulting fragment can be easily stored in pBR322 (PvuII-BamHI) as similarly described for bPRL.

EXAMPLE 8

Figure 4:
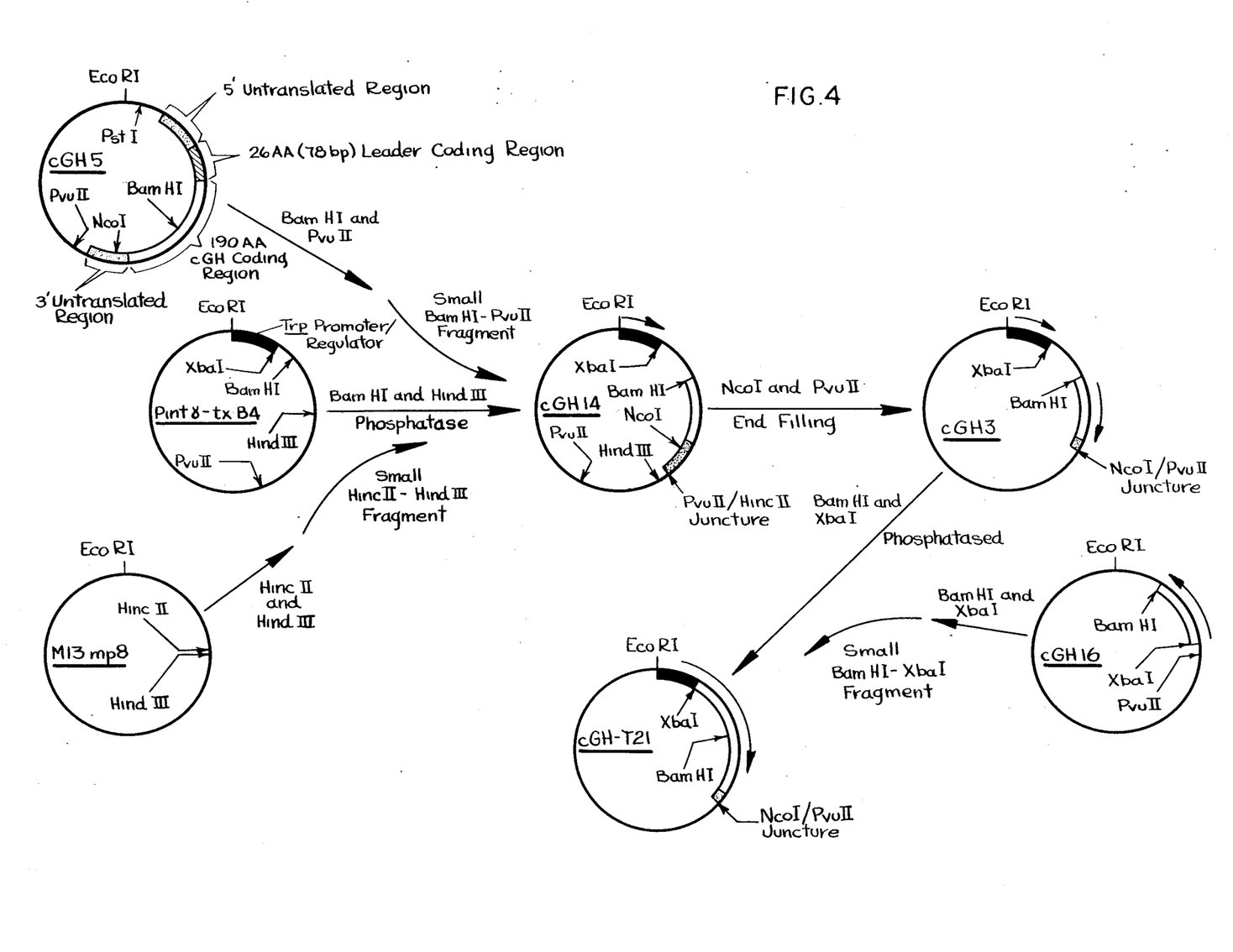

An expression vector is then constructed by a process generally consisting of incorporation of the 3' region of the cGH gene and a 5' region developed according to Example 7A (see FIG. 3). The construction process described below is illustrated in FIG. 4.

A pBR322-derived plasmid (Pint-γ-txB4) which contains a tryptophan (Trp) promoter sequence and an XbaI site 3' to a Shine/Delgarno sequence followed by a gene coding for γ-Interferon is used as the expression vector because it contains the necessary unique restriction sites to carry out the following constructions. The 3' end of the cGH gene is introduced into the expression vector by first cutting the vector at the unique HindIII and BamHI sites and the phosphatasing it (calf intestine phosphatase; Sigma). The vector is then ligated to sea plaque (Marine Colloids) purified cGH DNA (BamHI-PvuII small fragment derived from plasmid cGH5), as well as M13mp8 RF DNA which had been cut with both HindIII and HincII to provide a linker needed to join the PvuII end of the cGH5 DNA to the HindIII cut site of Pint-γ-txB4. The resulting colonies upon transformation (E.coli HB101) are screened by mini plasmid preparation with the appropriate enzymes to detect clones containing the BamHI-PvuII cGH fragment and the HindIII-HincII linker fragment from M13mp8 RF DNA. Clone cGH14 is isolated for further manipulations.

The next step in the construction involves removing as much as possible of the 3' untranslated portion of the clone (cGH14) and the copy number control region of the plasmid (located near the PvuII site). Clone cGH14 is cut with NcoI and PvuII (5 μl reaction). The reaction volume is then raised to 25 μl to end fill the NcoI end using Klenow in a standard sequencing buffer with 50 μm dNTP's at room temperature for 30 minutes. After completion of the reaction the DNA is phenol and chloroform extracted, then ethanol precipitated. The DNA is re-suspended in a standard ligase buffer and ligated with T$_4$ DNA ligase. The ligation reaction is transformed as before and colonies are screened for plasmids now lacking the NcoI-PvuII fragment.

One clone, cGH3, is used in the subsequent and final construction step. cGH3 DNA is cleaved with XbaI and BamHI, then phosphatased. This DNA is then ligated to cGH16 DNA (an end product of Primer A reaction described in Example 7A, FIG. 3, containing the 5' portion of cGH), digested with XbaI, BamHI and HaeIII. After transformation clones are screened for containing a complete cGH coding region by digestion with XbaI and BamHI. The plasmid from one clone, designated cGH-T21, containing a trp promoter regulator, an initial ATG, and the complete cGH coding region, is transformed into E.coli K-12 strain C600 (ATCC No. 39182) for expression analysis.

While the foregoing illustrative examples relate generally to the modification of a double-stranded cGH DNA sequence and a bPRL cDNA sequence, it will be apparent that such modifications may be made on any double-stranded DNA sequence. Additionally, it will be apparent that expression in yeast and other microorganism cells of such modified DNA sequences is also contemplated.

As one example, the methods of the present invention could easily have been superimposed on those illustrated in FIG. 4 of European Patent Application No. 054330, to develop a double-stranded cDNA sequence specifying a predominant portion of mature thaumatin but easily stored in pBR322. In the procedure illustrated in the application, after the step of modification of the 3' end of the portion of the preprothaumatin to delete protein coding regions beyond the terminal 5'-GCC-3' codon (specifying alanine) and to add a translation termination codon, modifications were performed at the 5' end. Specifically, a single-stranded primer of the sequence GCC ACC TCC GAG was employed to hybridize to the 5' sequence coding for the initial four amino acids of mature thaumatin and effect deletion of a multiple amino acid "leader" sequence. As indicated previously, the double-stranded DNA product of that procedure is not readily stored or amplified and must be promptly associated with a double-stranded linker by a separate reaction if it is to be inserted in an expression vector.

According to the present invention, a twelve base pair single-stranded primer having the sequence CTG CTC CTA CAC may be employed which is complementary to the base sequence toward the 5' end of the thaumatin-coding region beginning with the C in the codon for arginine at amino acid position 8 (base position +23). Note that the 5' end of the primer includes the base sequence CTG, providing the 3' half of a PvuII recognition site. The double-stranded sequence obtained as a product of polymerization of the hybrid sequence formed includes a half of a PvuII site making the sequence easily storable in pBR322. Alternatively, if a vector has a unique HpaI site, a primer beginning with the AAC of the asparagine codon (amino acid position 7) could be used as an alternative to the PvuII primer. AAC provides the 3' half of a HpaI restriction site.

Numerous other modifications and variations in the invention are expected to occur to those skilled in the art upon consideration of the foregoing description. Consequently, only such limitations as appear in the appended claims should be placed on the invention.

What is claimed is:

1. A method for selective modification of a double-stranded DNA sequence, comprising the steps:
   (1) forming a first selected single-stranded DNA copy of said double-stranded DNA sequence;
   (2) hybridizing said first selected single-stranded copy to a manufactured DNA sequence which comprises
      (a) a single-stranded portion complementary to a selected portion of said first selected single-stranded copy, and
      (b) a double-stranded portion having a free end and an end wherein one strand is joined to the single-stranded portion, which double-stranded portion includes base pairs forming a recognition site for cleavage by a restriction endonuclease enzyme or includes at its free end base pairs forming half of a recognition site for cleavage by a blunt-end-forming restriction endonuclease;
   (3) incubating the hybridized product of step (2) with nucleotide triphosphates and DNA polymerase under conditions facilitative of 3' extension of the single-stranded portion of said manufactured sequence with bases complementary to said first selected single-stranded DNA copy, so that said double-stranded DNA sequence is reconstructed except for that portion of its sequence 3' to the site of hybridization of the selected single-stranded copy to the 5' end of the single-stranded portion of said manufactured sequence;
   (4) treating the product of step (3) to delete single-stranded sequences 3' to the site of hybridization of the selected single-stranded copy to the 5' end of the single-stranded portion of said manufactured sequence; and
   (5) recovering the modified double-stranded DNA sequence.

2. The method according to claim 1 further comprising the steps:
   (6) forming a second selected single-stranded DNA copy of said modified double-stranded DNA sequence of step (5), said second selected single-stranded DNA copy being the partial complement of said first selected single-stranded copy of step (1); and
   (7) repeating steps (2), (3), (4), and (5) on said second selected single-stranded copy of step (6).

3. The method according to claim 1 wherein said double-stranded portion of said manufactured DNA sequence includes a sequence coding for

5'-ATG-3'
3'-TAC-5'.

4. The method according to claim 1 wherein said first selected single-stranded copy of step (1) is the plus strand of said double-stranded DNA sequence.

5. The method according to claim 1 wherein said first selected single-stranded copy of step (1) is the minus strand of said double-stranded DNA sequence.

6. The method according to claim 1 wherein said 5' end of said double-stranded portion of said manufactured DNA sequence comprises bases providing the 3' end of a blunt-ended restriction site selected from the group consisting of: PvuII, HpaI, BalI, SmaI, HaeIII, AluI, NaeI, and StuI.

7. The method according to claim 1 wherein said manufactured DNA sequence comprises a range of from about 10 to about 20 bases forming said single-stranded portion and from about 10 to about 20 base pairs forming said double-stranded portion.

8. The method according to claim 1 wherein said first selected single-stranded DNA copy is formed by denaturation of said double-stranded DNA sequence.

9. The method according to claim 1 wherein said first selected single-stranded DNA copy is formed by a single-stranded filamentous bacteriophage.

10. The method according to claim 2 wherein said first selected single-stranded DNA copy is formed by a single-stranded filamentous bacteriophage.

11. The method according to claim 10 wherein said second selected single-stranded DNA copy is formed by a single-stranded filamentous bacteriophage.

12. The method according to claim 1 wherein S1 nuclease is employed in said treatment for deletion of single-stranded regions.

* * * * *

UNITED STATES PATENT AND TRADEMARK OFFICE
CERTIFICATE OF CORRECTION

PATENT NO. : 4,666,839
DATED : May 19, 1987
INVENTOR(S) : LAWRENCE M. SOUZA

It is certified that error appears in the above-identified patent and that said Letters Patent is hereby corrected as shown below:

Col. 5, line 29, after "include" insert --a--

Col. 6, line 64, after "FIG. 1" insert --selection--

Col. 8, line 28, delete "oocur" and insert --occur--

Col. 10, line 1, after "wherein" insert --the--

Col. 11, line 27, delete "sequence" and insert --sequences--

Col. 17, line 64, delete "to"

Col. 18, line 55, delete "5'-TCC" and insert --5'-TTC--

Col. 20, line 27, delete "the" and insert --then--

Signed and Sealed this

Fifteenth Day of January, 1991

*Attest:*

HARRY F. MANBECK, JR.

*Attesting Officer*   *Commissioner of Patents and Trademarks*